United States Patent [19]

Callebert

[11] Patent Number: 5,527,582
[45] Date of Patent: Jun. 18, 1996

[54] FLOOR COVERING AND/OR WALL COVERING PRODUCTS HAVING AN ACARICIDAL EFFECT, AND PROCESS FOR OBTAINING THESE

[75] Inventor: Franck Callebert, Englos, France

[73] Assignee: Sommer S.A., Nanterre, France

[21] Appl. No.: 119,132

[22] PCT Filed: Mar. 20, 1992

[86] PCT No.: PCT/EP92/00644

§ 371 Date: Jan. 21, 1994

§ 102(e) Date: Jan. 21, 1994

[87] PCT Pub. No.: WO92/16683

PCT Pub. Date: Oct. 1, 1992

[30] Foreign Application Priority Data

Mar. 21, 1991 [EP] European Pat. Off. .............. 91200636

[51] Int. Cl.⁶ ...................................................... B32B 9/00
[52] U.S. Cl. .................................. 428/95; 428/85; 428/96; 428/357; 428/372; 428/378; 428/394; 428/395; 428/907; 424/403; 424/404; 424/405; 424/407
[58] Field of Search ...................... 428/195, 395, 428/372, 378, 95, 85, 96, 76, 357, 394, 907; 424/403, 404, 405, 407

[56] References Cited

U.S. PATENT DOCUMENTS 3,857,934  12/1974  Bernstein .................................. 424/30
5,024,840   6/1991  Blakely .................................... 424/404

FOREIGN PATENT DOCUMENTS 63-308149   6/1987  Japan .
62-158201   7/1987  Japan .
 2142705    5/1990  Japan .
870144942   2/1991  Japan .
 3031206    2/1991  Japan .
 1224304    4/1991  Japan .
WO90/14107 11/1990  WIPO .

OTHER PUBLICATIONS

Chemical Abstracts, vol. 113, No. 11, Sep. 10, 1990, U.S., abstract No. 93315W & JP-A-0268364 (NIPPON TERPENE), p. 278.

Primary Examiner—Patrick J. Ryan
Assistant Examiner—Abraham Bahta
Attorney, Agent, or Firm—Chilton, Alix & Van Kirk

[57] ABSTRACT

The present invention relates to textile-based floor covering or wall covering products endowed with acaricidal properties provided with a backing comprising a polymer matrix containing one or more acaricides as well as a carrier for the acaricides.

10 Claims, 3 Drawing Sheets

FLOOR COVERING AND/OR WALL COVERING PRODUCTS HAVING AN ACARICIDAL EFFECT, AND PROCESS FOR OBTAINING THESE

SUBJECT OF THE INVENTION

The present invention relates to textile-based floor covering or wall covering products endowed with acaricidal properties.

The invention also encompasses the processes of preparation of these products.

STATE OF THE ART

It is known, from the work of Voorhorst and Spiekssma, that numerous so-called house dust allergies are caused by acarids. A relatively complete bibliography on the subject has appeared in the article by J.E.M.H. van Bronswijk: "Hausstaubmilben, Vorkommen und Bedeutung" ("House dust mites, occurrence and significance") in Allergologie, 1, No. 2, 1978, p. 55. It is known that the pyroglyphid acarids, essentially represented by Dermatophagoïdes pteronyssinus, Dermatophagoïdes farinae and Euroglyphus maynei, derive their nourishment from human and animal squamae (dead skin, debris of nails, fur and feathers): the daily loss per individual of 70 to 140 mg of squamae permits several thousands of acarids to live for several months. Furthermore, mould growths form part of their biotopes, because these provide them with a supply of vitamins and permit predigestion of the squamae. They live in areas where their nourishment is to be found, that is to say in places where man rests, under optimum conditions of atmospheric humidity (80% relative humidity) and of temperature (25° C.), and in the absence of light, because they are sensitive to solar UV. The pyroglyphid acarids, whether dead or alive, are allergizing. This is also true of their excrement and their teguments. Consequently, any treatment of the environment of patients who are allergic to acarids must involve an acaricidal treatment.

Recent studies of the effect of acarids have been published by Platts-Mills and Chapman in J. Allergy Clin. Immunol., 80., Dec. 6, 1987, p. 755 and by E. Bischoff: Méthodes actuelles de quantification des acariens dans l'habitat (Current methods of quantifying acarids in the habitat), Rev. fr. Allergol., 1988, 28 (2), pp. 115–122.

Whilst bedding is the place which conceals the largest number of acarids, squamae of human and animal origin are to be found copiously on the floor surface and especially in the floor coverings and/or wall coverings such as pile carpets and wallpapers, which consequently constitute a secondary proliferation medium for the acarids.

In the present text, a textile floor covering or wall covering is to be understood as a covering obtained by shaping a textile material, for example a yarn, fibre or flock by techniques known per se, for example by tufting or needlepunching, but also by the so-called verticalization techniques described in the publication WO 91/00382 or by the techniques described in the Patents FR-8 607 842 and EP-0 811 460, which involve an ultrasonic welding process.

In order to fix the textile fibres so as to ensure dimensional stability and so as to meet the comfort requirements, the floor coverings and/or wall coverings as described above are provided, on the back, with a layer which is generally deposited by coating and which forms a polymeric backing hereinafter referred to as a polymer matrix. It also performs a number of other functions such as heat and sound insulation, increase in mechanical strength, etc.

It should be noted that in the case of the textile floor coverings and/or wall coverings obtained by the conventional tufting processes as well as those obtained by the verticalization or ultrasonic welding techniques, the backing also comprises a nonwoven, preferably of polyethylene terephthalate (PET), which may accordingly be involved in the definition of the backing.

For these reasons, the backing referred to as a polymer matrix is generally composite and often consists of several superposed layers.

The most widely used products for forming the backing are matrices of plasticized PVC, polyurethane foams or latices of the styrene-butadiene type and optionally combinations of these, more generally in combination with other materials such as nonwoven webs or glass webs.

By virtue of their configuration, the textile floor coverings and/or wall coverings, in particular the products mentioned above, in fact permit retention of the squamae on which the acarids feed. They furthermore constitute a medium which at one and the same time excludes light, undergoes no major air movement and is at a stable temperature and a stable humidity, which favours the development of the acarids. Contrary to bedding, this type of medium is difficult to treat because it is fixed and difficult to clean in depth.

It should be noted that the acarids, contrary to the clothes moths (commonly called mites), do not feed on the textile materials which constitute their life environment. Hence, treating the textile fibres in order to impart to them an acaricidal effect through ingestion, as is carried out, for example, with anti-mite treatments, will not work.

Of course there are numerous acaricidal products for application by spraying or by shampooing, which however only exhibit short-duration effects. Furthermore, during conventional maintenance operations (vacuum-cleaning, shampooing or injection/extraction), they are removed and in any case they do not act on the site where the acarids are located. Commercial products of this type are sold under the name ACARDUST, ALLERBIOCID and ACAROSAN (registered trade marks).

Paints have also been proposed which possess an acaricidal effect and carrying the name ARTILIN, produced by the company 3A (Les Cahiers Techniques du Bâtiment, No. 116, April, 1990, p. 155).

Solutions aiming to achieve a diffusion of insecticidal or anti-parasitary substance into a turbulent medium have also been described, especially in the documents EP-A-0 211 207 and EP-A-0 338.821.

The document JP-A-0 268 364 describes the use of a powder prepared from dextrin and menthone. This powder, which exhibits delayed evaporation effects, is introduced into a resin which is itself used as a surface coating on textile coverings. It is obvious that this acaricide has the disadvantage that it is easily removed during conventional maintenance operations and accordingly does not provide a lasting solution.

The document JP-A-2 142 705 describes the use of molecules such as benzoic, salicylic and dehydroacetic acids (which are not acaricides and which are small molecules), intended to be sprayed onto garments, carpets or the like.

The document JP-A-62 153 201 describes a solution according to which a carpet or a tatami is fixed to the floor with an adhesive which contains an acaricide. In particular, this solution is not intended for floor coverings and/or wall coverings which have a backing in the form of a polymer matrix. Furthermore, it is impossible to place such coverings loosely on the floor when using the solution proposed in this document.

The document JP-A-63 308 149 describes the use of a sheet of paper made of a conventional nonwoven, which is porous and impregnated with an acaricidal preparation intended for the protection of Japanese mattresses.

The document JP-A-3 031 206 describes the formulation of a curative treatment intended for mattresses and tatamis and allowing the acarids and other insects to be destroyed.

The document JP-A-1 224 304 describes a preparation containing a pyrethinoid which can be vaporized or spread in various parts of a home and in particular onto carpets.

The document WO-A-9014107 describes the use of phosphoric acid esters in preventing the development of bacteria and microbes in fitted carpets. This document does not provide a solution to the problem of allergies caused specifically by acarids.

It should furthermore be noted that numerous insecticidal products have poor acaricidal properties.

None of the references cited provides, or suggests, a long-lasting solution to the allergy hazards which are presented by the development of acarids in modern textile-based floor coverings or wall coverings provided with a backing comprising a polymer matrix, such as fitted carpets, etc.

In particular, they essentially concern curative solutions which are only employed when allergy phenomena are observed. The implementation of such solutions most commonly requires substantial quantities of active products which sometimes themselves cause allergies or secondary intolerances as a result of the high concentration of these products in the atmosphere.

ENVISAGED OBJECT OF THE PRESENT INVENTION

The principal object which the present invention addresses is to provide a textile-based floor covering and/or wall covering which is treated so as to impart to it preventive acaricidal properties these being of long duration, in particular durations of the order of several years.

PRINCIPAL CHARACTERISTIC FEATURES OF THE INVENTION

The present invention relates to textile-based floor covering and/or wall covering products provided with a backing comprising a polymer matrix, characterized in that the said polymer matrix contains one or more acaricides as well as a carrier for the said acaricides.

These covering products essentially consist of textile fibres which have been tufted or needle-punched or verticalized or ultrasonically welded onto a nonwoven support provided with a polymer matrix.

The carrier is a constituent usually present in the composition of the polymer matrix, such as, for example, a plasticizer for a PVC matrix or a surfactant for a latex-based matrix. It is preferably chosen as a function of its good adhesive properties.

The other characteristics and advantages of the present invention will emerge from the description which follows.

SOLUTION PROPOSED BY THE INVENTION

The solution provided by the present invention is based on observation of the migration and volatility properties of certain constituents present in the composition of the polymer matrix of the backing, and on the fact that these constituents and in particular the plasticizers or surfactants usually present in the polymer matrix are capable of carrying with them low amounts of acaricides if the latter have an affinity towards their carrier.

In the case of backings produced from a polymer matrix, the two phenomena of migration and volatility are simultaneous and concurrent. These phenomena govern the vertical concentration of the agents used as plasticizers and/or surfactants. The volatility only affects the upper layer in contact with the atmosphere, whilst the migration affects all the layers of the polymer matrix complex.

Figure 1:
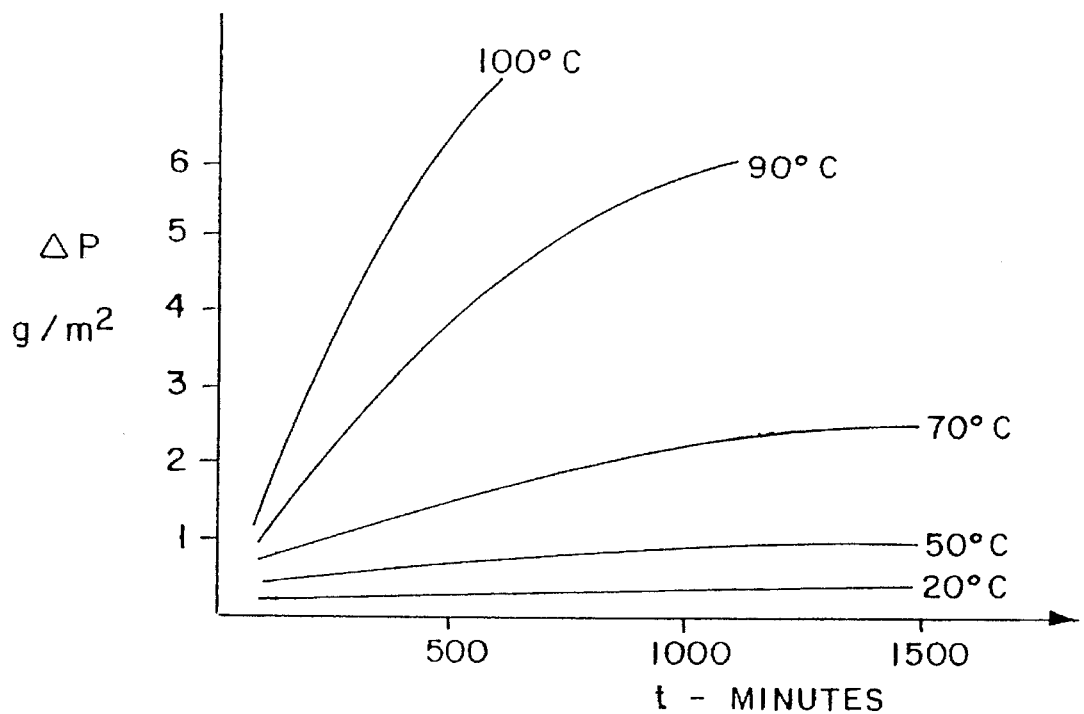
FIG. 1 represents, for various temperatures, the volatility of a conventional plasticizer, expressed in % weight loss as a function of time.

In particular, studies have shown that the volatility of the plasticizers or surfactants depends on the concentration of these in the pure state or in a mixture, on their nature, on the composition of the mixtures, on the contact time with the atmosphere, and on the turbulence and temperature of the air close to the surface. The volatility curves of a conventional plasticizer as a function of time, for various temperatures, are as shown in FIG. 1.

The principal property utilized in the present invention is that the volatility of certain plasticizers or surfactants depends on the concentration of these in the polymer matrix, the latter acting like a sponge for low amounts of plasticizer or surfactant.

Figure 2:
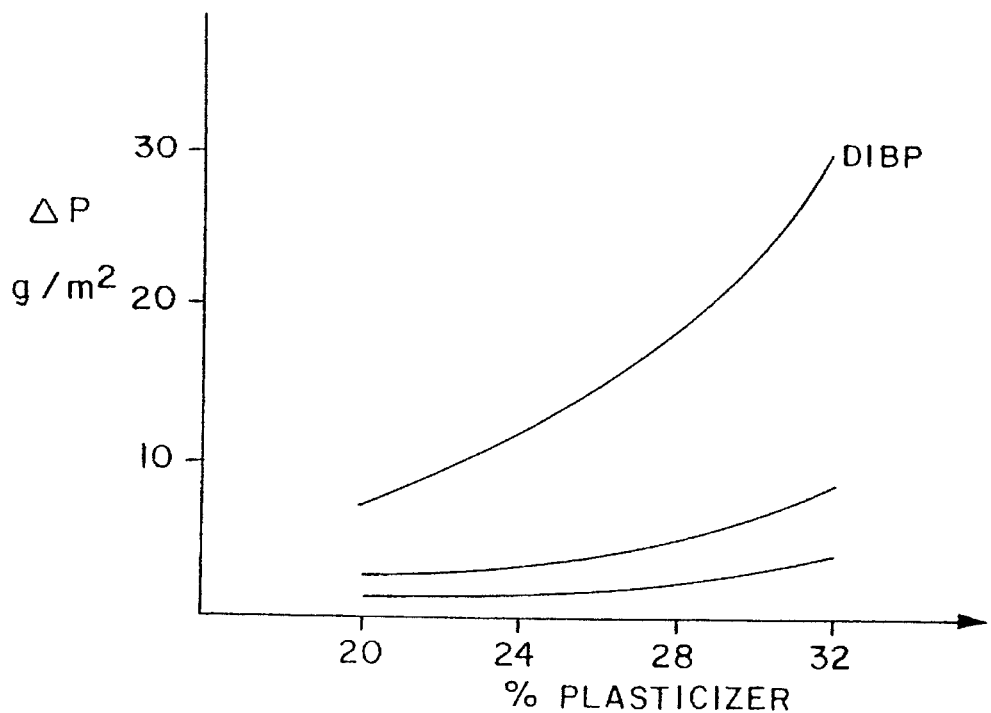
FIG. 2 represents the volatility of various usual plasticizers as a function of the concentration of the plasticizer in the calendered film which constitutes the polymer matrix.
Figure 3:
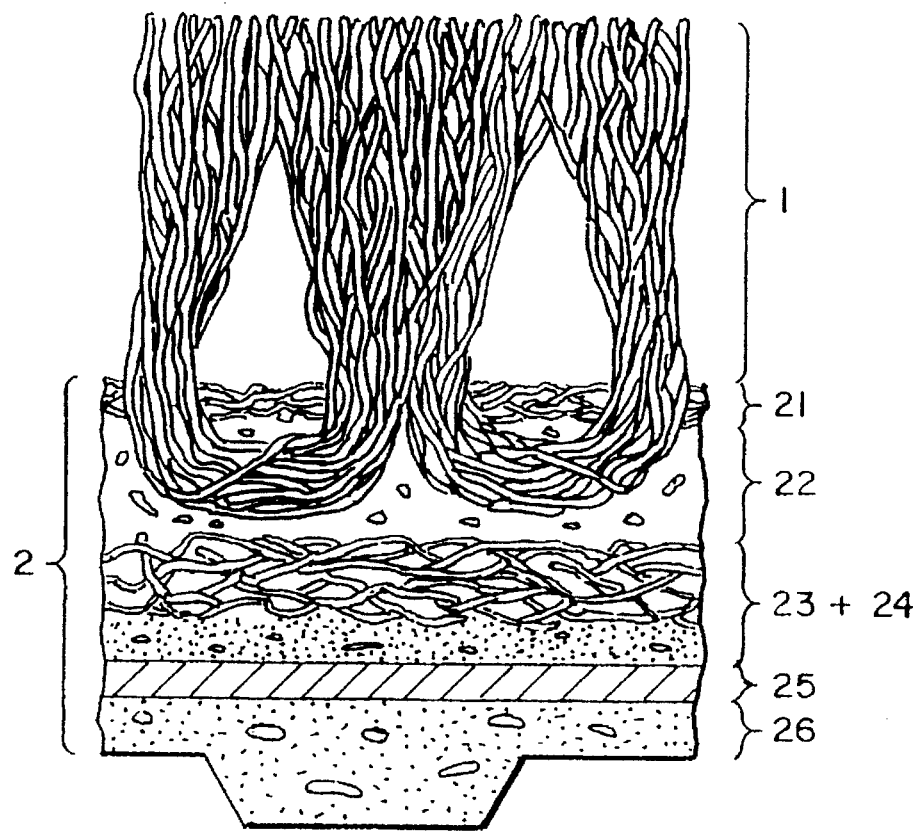
FIG. 3 represents a schematic cross-section of a floor covering of the tufted type, having, as its backing, a structure suitable for cutting into tiles, and based on PVC, to which backing the treatment of the invention can be applied.
Figure 4:
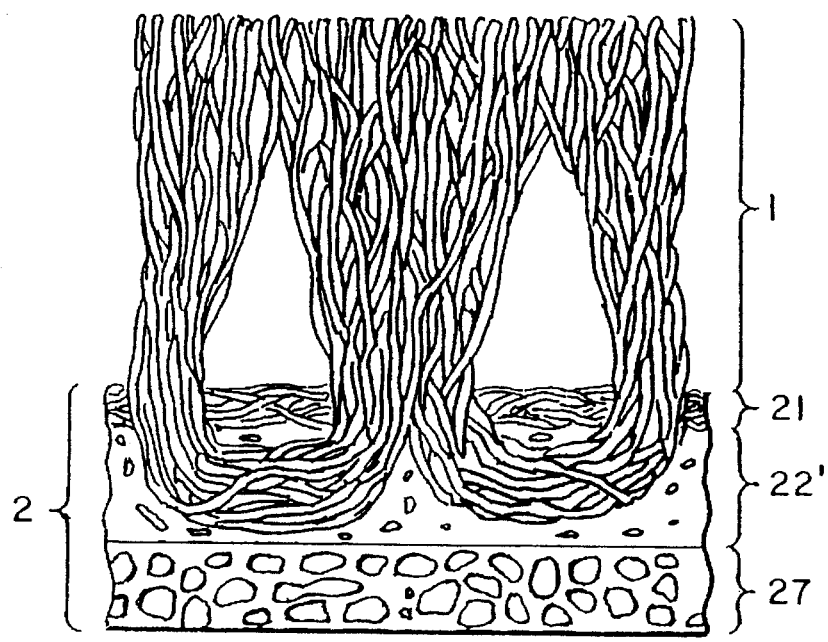
FIG. 4 represents a schematic cross-section of a floor covering of the tufted type, having, as its backing, a structure of the styrene-butadiene foam type.
Figure 5:
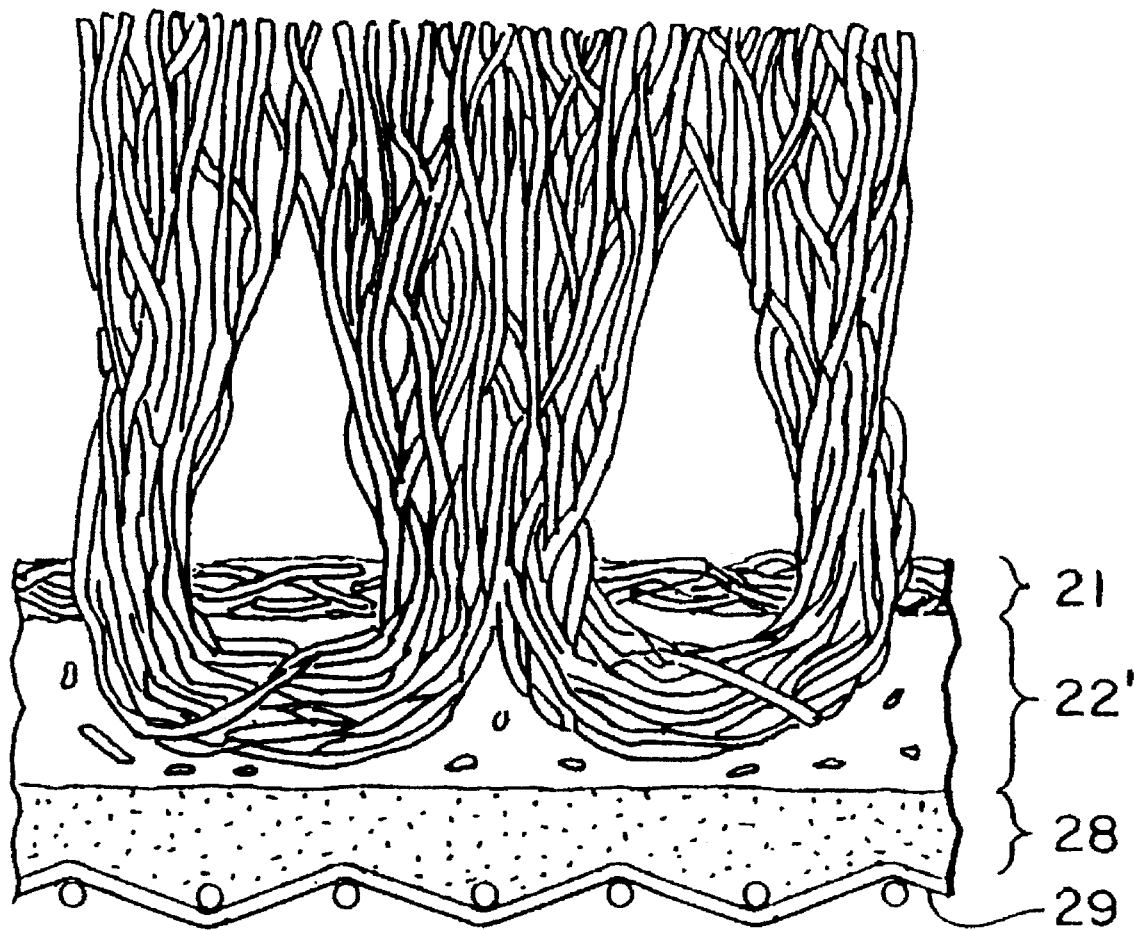
FIG. 5 represents a schematic cross-section of a floor covering of the tufted type, having, as its backing, a styrene-butadiene resin structure with a fabric backing.

This property may be seen from FIG. 2, which shows the volatility of certain plasticizers as a function of the concentration in a calendered film.

On this concentration also depend the migratory properties of certain plasticizers, which tend to regulate and equilibrate their concentration in the various layers.

The migration phenomena generally manifest themselves in the case of molecules which have low compatibility with the polymer matrix, that is to say which, for reasons of polarity, molecular weight or chemical structure, exhibit little affinity for this polymer matrix. Certain plasticizers, such as those of the phthalate type which have been mentioned above, are widely used for PVC, and the surfactants, generally tensides, are present in latices of, for example, the styrene-butadiene type.

The precise adjustment of the amount of certain plasticizers or surfactants capable, by virtue of affinity, of carrying the acaricides with them, makes it possible to increase the volatility of the plasticizers or surfactants and acaricides in a non-turbulent medium (stagnant air at the bottom of the carpeting) and hence create a local concentration difference at the surface, bringing about the migration of the plasticizer (or surfactant)/acaricide complex located deeper down. A system of releasing a constant amount is thus created, making it possible to adjust the amounts to be released and hence the persistence time.

Furthermore, the products applied to the backing of the textile in order to produce the polymer matrix must necessarily contain a series of products required for their use and referred to as processing aids (that is to say processing adjuvants or use adjuvants) which intrinsically possess properties of migrating over a period of time.

This property is advantageously utilized, in an inventive manner, in order to impart long persistence times if an acaricidal product is incorporated into the polymer matrix which constitutes the backing of the floor covering and/or wall covering, according to the invention.

In the case of the products obtained by the conventional tufting processes or by the processes referred to as verticalization or ultrasonic welding, the polymer matrix can consist of a coating of the nonwoven used as the support for the textile fibres.

In this way, the present invention advantageously makes it possible to achieve slow and constant release, and to have the possibility of causing the required and sufficient amount of a contact acaricide to reach the site where the acarids develop, to form an acaricide reserve in the polymer matrix and, through the release of the surfactants or plasticizers which have adhesive properties, to contribute to a locking-in the bodies, teguments and excretions of the acarids, thus preventing their becoming resuspended in the atmosphere during cleaning operations, in particular during vacuum cleaning.

This original solution has not been proposed in the prior art and it is unexpected that it can impart persistence of the order of several years.

The concentration of acaricide need not be high. Release amounts of the order of a few parts per million to a few hundreds of parts per million (ppm) at the site where the acarids proliferate are often adequate. Such values can be achieved by incorporating contents of the order of 0.1 to 10% by weight of the backing layer into which the acaricides are incorporated. It should be noted in this respect that it is not necessary to incorporate the acaricides into the entire mass of the backing. In particular, in the case of a composite backing, the presence of the acaricides in one part of the backing, preferably that which is close to the textile part, for example at the base of the tufted or needle-punched part, suffices.

The acaricides employed can be those currently recommended and commercially available. It appears particularly advisable to employ light-stable compounds and/or to incorporate known light stabilizers (especially UV stabilizers) such as the stilbene derivatives or others, together with the acaricide.

The pyrethrenoids of the "methrin" type, such as: cypermethrin, deltamethrin, 5-(phenylmethyl)-3-furanylmethyl (1R,trans-(+)-2,2-dimethyl-3-(2-methyl-1-propenyl)cyclopropane-carboxylate (bioresmethrin) and permethrin are particularly suitable, as are compounds of the benzene-acetate type such as cyano-(3-phenoxybenzyl)methyl 4-chloro(α)-(1-methylethyl)benzene-acetate (fenvalerate) or organophosphorus compounds such as dibrom, endosulfan or chlorfenvinphos. A certain number of these products are described in the documents EP-A-0 211 207 and EP-A-0 330 821 incorporated by reference in the present descriptive note. As has furthermore already been described in these documents, according to the invention it is also possible to employ the molecules possessing acaricidal activity in association with "synergists" which increase their activity.

The invention also relates to a process for the production of a floor covering and/or wall covering in which there is applied, onto a textile base produced especially by the techniques already mentioned, a backing consisting of a polymer matrix, the process being characterized in that the said polymer matrix contains one or more acaricides.

According to this process, the acaricides are preferably added to the preparation, which is to be applied as a backing, simultaneously with, or after, the plasticizers and/or the surfactants.

It has in fact been found that the acaricides can be incorporated without difficulty in the formulations usually employed for the backings of the covering. It is generally advisable to add them simultaneously with, or after, the plasticizers and/or the surfactants, that is to say the substances whose migratory properties are well known in polymer matrices and in particular in the backings of textile coverings.

DESCRIPTION OF SEVERAL PREFERRED EMBODIMENTS OF THE INVENTION

A typical example of a floor covering is illustrated in FIG. 3.

This covering consists essentially of a textile part (consisting of natural or synthetic fibres), which carries the general reference 1, and is in the form of, for example, a tufted product (velour or loop pile) on a composite backing which carries the general reference 2. The fibres "emerge" more or less vertically relative to this backing.

In the first example chosen, this backing 2 consists of a nonwoven 21, preferably of polyethylene terephthalate (PET), having a weight per unit area of 120 $g/m^2$, of a PVC matrix (precoat) 22 having a weight per unit area of 800 $g/m^2$, of a glass web 23 combined with a so-called "complexing" layer of PVC, 24, which has a total weight per unit area of 400 $g/m^2$, of a calendered film 25 having a weight per unit area of 500 $g/m^2$ and, finally, of a PVC bottom layer 26, preferably embossed, having a weight per unit area of 1500 $g/m^2$.

According to other embodiments represented in FIGS. 4 and 5, the backing 2 can consist of a nonwoven 21 and a styrene-butadiene latex precoat 22', on which there is provided either a single foam latex coating (see FIG. 4) or a double-layer latex coating 28 and a backing web 29 (see FIG. 5).

The fibres which constitute the textile part 1 are held in the PVC matrix 22 or latex matrix 22'. Near the surface of the nonwoven 21, between the textile fibres, there forms a medium for the propagation and development of the acarids, resulting from the nutrition supply consisting of the squamae which drop onto the floor covering and which pass between the fibres and accumulate on the surface of the backing. The interlaced fibres protect this medium from light and from air circulation, and stabilize the temperature.

The acaricide is incorporated into the body of the backing and preferably in the vicinity of the environment which favours the development of the acarids, namely into the nonwoven 21 and/or into the PVC matrix 22 or latex matrix 22'. The acaracides can be, for example, pyrethrenoids, carbamates, organophosphorus compounds and/or organohalogen compounds.

FORMULATION EXAMPLES

The invention will be described in more detail, by way of illustration and without implying a limitation, with the aid of three formulation examples of the invention (the proportions and percentages are expressed by weight).

Example 1: PVC backing for a textile tile

The following are incorporated successively into 100 parts of polymer:

| Plasticizers | |
| --- | --- |
| BBP | 4 to 6% |
| DDB (dodecylbenzene) | 10 to 15% |
| DIMP (diisomethyl phthalate) | 15 to 20% |
| Filler | 50 to 60% |
| Stabilizer | 0.4 to 2% |
| Acaricides | |
| Pyrethrenoids | 0.3 to 1.2% |
| and/or | |
| Organophosphorus compounds | 0.5 to 1.5% |
| and or | |
| Carbamates | 1.0 to 3.0% |
| Synergist | |
| Piperonyl butoxide | 5 to 10% |
| Coating on a three-roll stack at 900 g/m² | |

Example 2: Backing for an SBR-type support

| | |
| --- | --- |
| SBR latex | 15 to 20% |
| Antifoaming agent | 0.01 to 0.1% |
| Thickener | |
| Carboxymethylcellulose CMC | 30 to 35% |
| Water | 45 to 50% |
| Synergist | |
| Piperonyl butoxide | 3 to 7% |
| Acaricides | |
| Pyrethrinoids | 0.4 to 2.6% |
| Organophosphorus compounds | 0.6 to 3% |
| Wetting agent | 0.2 to 0.4% |
| Knife-coating at 500 g/m² | |

Example 3: Formula for the coating of the nonwoven

| | |
| --- | --- |
| SBR latex | 30 to 40% |
| Dispersant | 0.2 to 0.4% |
| Antifoaming agent | 0.02 to 0.1% |
| Thickener | |
| Carboxymethylcellulose CMC | 40 to 60% |
| Adjuvant | 1 to 1.5% |
| Synergist | |
| Piperonyl butoxide | 3 to 5% |
| Acaricides | |
| Pyrethrinoids | 1 to 5% |
| Organophosphorus compounds | 3 to 7% |
| Knife-coating at 25 g/m² | |

I claim:

1. A cover material for at least one of a wall and a floor, comprising:

a textile base, a backing supporting the base, the backing including a polymer matrix comprising at least one acaricide selected from the group consisting of pyrethrenoids, carbamates, organophosphorus compounds and organohalogen compounds, and a carrier for the at least one acaricide, said carrier possessing migration properties, and possessing adhesive properties in order to fix acarids.

2. A cover material according to claim 1, wherein the at least one acaricide is used conjointly with at least one of a photostabilizer and a synergist.

3. A cover material according to claim 1, wherein the at least one acaricide is contained in a part of the polymer matrix, and said part contains 0.1 to 10% by weight acaricide.

4. A cover material according to claim 1, wherein the carrier is at least one of a plasticizer and a surfactant.

5. A cover material according to claim 1, wherein the backing includes a non-woven support and the polymer matrix is formed on the non-woven support.

6. A cover material according to claim 5, wherein the textile base comprises textile fibers which are tufted, needle punched, verticallized, or ultrasonically welded onto the non-woven support.

7. A cover material according to claim 5, wherein the non-woven support has a polymer precoat formed thereon.

8. A cover material according to claim 7, wherein the precoat comprises at least one member selected from the group consisting of polyvinyl chloride and styrenebutadiene latex.

9. A cover material according to claim 5, wherein the non-woven support comprises polyethylene terephthalate.

10. A cover material for at least one of a wall and a floor, comprising:

a textile base, a backing supporting the base, the backing including a polymer matrix comprising at least one acaricide and a carrier for the at least one acaricide, said carrier possessing migration properties, and possessing adhesive properties in order to fix acarids.

* * * * *